US00PP20358P2

(12) United States Plant Patent
Moore

(10) Patent No.: US PP20,358 P2
(45) Date of Patent: Sep. 29, 2009

(54) ***COTINUS* PLANT NAMED 'DUSKY MAIDEN'**

(50) Latin Name: *Cotinus szechuanensis xcoggygria*
Varietal Denomination: Dusky Maiden

(76) Inventor: Peter Moore, 1 Valley View, Longstock, Stockbridge, Hampshire (GB) SO20 6EF ( * ) Notice: Subject to any disclaimer, the term of this patent is extended or adjusted under 35 U.S.C. 154(b) by 0 days.

(21) Appl. No.: 12/221,643

(22) Filed: Aug. 4, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent L Bell

(57) ABSTRACT

A new and distinct cultivar of *Cotinus coggygria* plant named 'DUSKY MAIDEN' with bushy plant habit and bright red-purple foliage when exposed to full sunlight. In partial shade, the foliage color remains green-purple. The leaves of 'DUSKY MAIDEN' bear undulating leaf margins and the leaf veins and petioles are redder than the red-purple leaf blade. The inflorescence of 'DUSKY MAIDEN' appears smoky due to the presence of numerous light purple hairs which grow along the entire length of the pedicels.

4 Drawing Sheets

Genus: *Cotinus.*

Species: *szechuanensis×coggygria.*

Denomination: 'DUSKY MAIDEN'.

BACKGROUND OF THE INVENTION

The present invention relates to a new and distinct cultivar of Smoke Bush known botanically as *Cotinus szechuanensis× coggygria* and referred to hereinafter by the cultivar name 'DUSKY MAIDEN'.

'DUSKY MAIDEN' is a seedling selection made in 1997 and arising from the inventor's controlled cross-pollination of *Cotinus coggygria* 'Velvet Cloak' (unpatented) as the male parent and an unnamed *Cotinus szechuanensis* (species, unpatented) as the female parent. The invention was carried out and tested in the inventor's nursery and garden in Hampshire, United Kingdom.

'DUSKY MAIDEN' is a bushy plant suitable for use in the landscape or in a container on the patio. It is grown for its foliage color which is bright red-purple when exposed to full sun. The leaves of 'DUSKY MAIDEN' have wavy edges.

'DUSKY MAIDEN' has red-purple leaves and differs from its female parent, *Cotinus szechuanensis* which has green leaves. 'DUSKY MAIDEN' has undulate leaf margins which differ from its male parent *Cotinus* 'Velvet Cloak' whose leaf margins are flat. The closest known comparison plants known to the inventor are *Cotinus* 'Grace' (unpatented) and *Cotinus* 'Royal Purple' (unpatented). 'Grace' is a vigorous tall shrub with large purplish-red flowers growing in large clusters whereas 'DUSKY MAIDEN' is more compact with smaller leaves and undulate leaf margins. 'DUSKY MAIDEN' is comparable in color to 'ROYAL PURPLE' but produces fewer flowers, roots more easily from cuttings, and has a more compact bushy plant.

The first asexual propagation was carried out by the inventor in 1998 at the inventor's nursery in Hampshire, United Kingdom, using softwood cuttings. Since that time under careful observation, 'DUSKY MAIDEN' has been determined stable, uniform, and reproduces true to type in successive generations of asexual propagation.

An application for European Plant Breeders Rights, Application Number 2007/1446 was filed on June 6, 2007. However such applications are not published at the time of filing. The application was first published in the official gazette of the European Community Plant Variety Rights Office on Aug. 15, 2007.

SUMMARY OF THE INVENTION

The following characteristics represent the distinguishing traits of the new variety of *Cotinus* named 'DUSKY MAIDEN':

1. 'DUSKY MAIDEN' is a bushy form of *Cotinus*, especially when grown in containers.
2. The foliage of 'DUSKY MAIDEN' is bright red-purple when exposed to full sunlight. In partial shade, the foliage color will remain green-purple.
3. The foliage of 'DUSKY MAIDEN' exhibits undulating leaf margins, and the leaf veins and petioles are redder than the red-purple leaf blade.
4. The inflorescence of 'DUSKY MAIDEN' exhibits a smoky appearance after petal drop. This effect is caused by the presence of numerous light purple hairs which grow along the entire length of the pedicels.
5. 'DUSKY MAIDEN' is deciduous and is hardy at least to USDA Zone 7. Further tests will be required in order to establish hardiness in colder zones.

BRIEF DESCRIPTION OF THE DRAWINGS

The accompanying colored photographs illustrate the overall appearance of the new variety.

The drawing labeled

The drawing labeled

The drawing labeled

The drawing labeled

Figure 1:
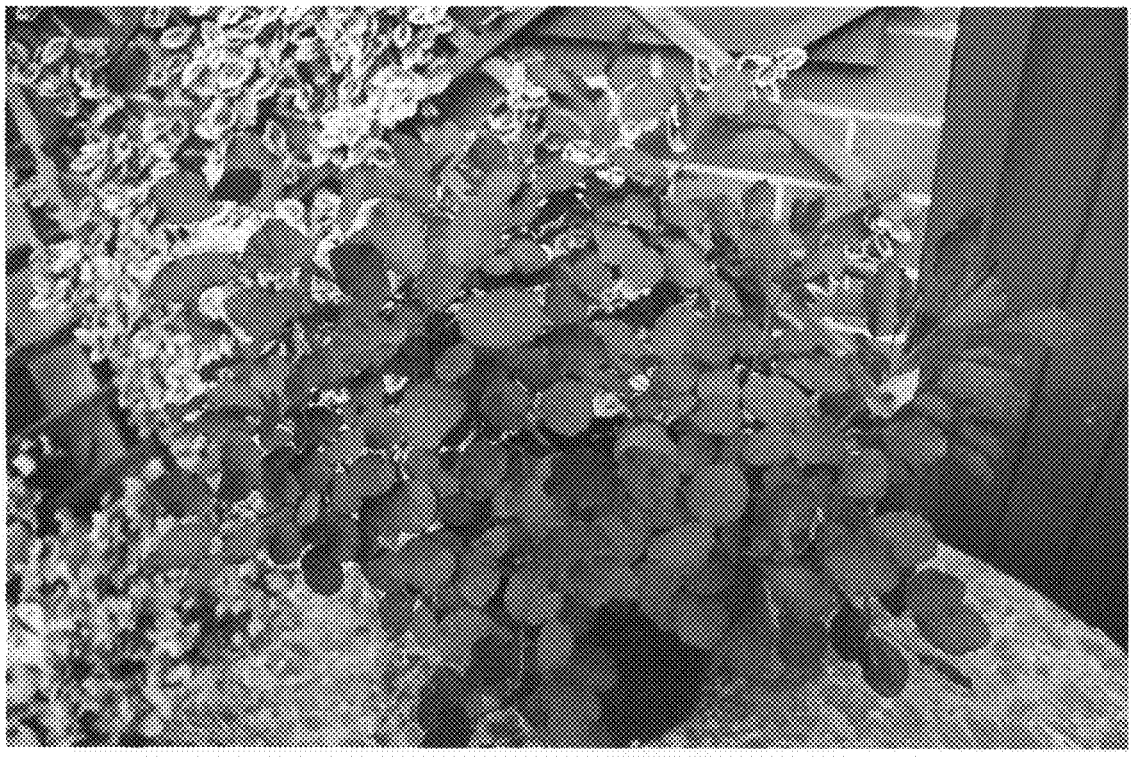
FIG. 1 illustrates a whole plant of 'DUSKY MAIDEN' which has been grown in partial shade in a 3 liter container at the inventor's nursery in Hampshire, United Kingdom. The drawing illustrates the purplish color of the new growth which has received more sunlight.
Figure 2:
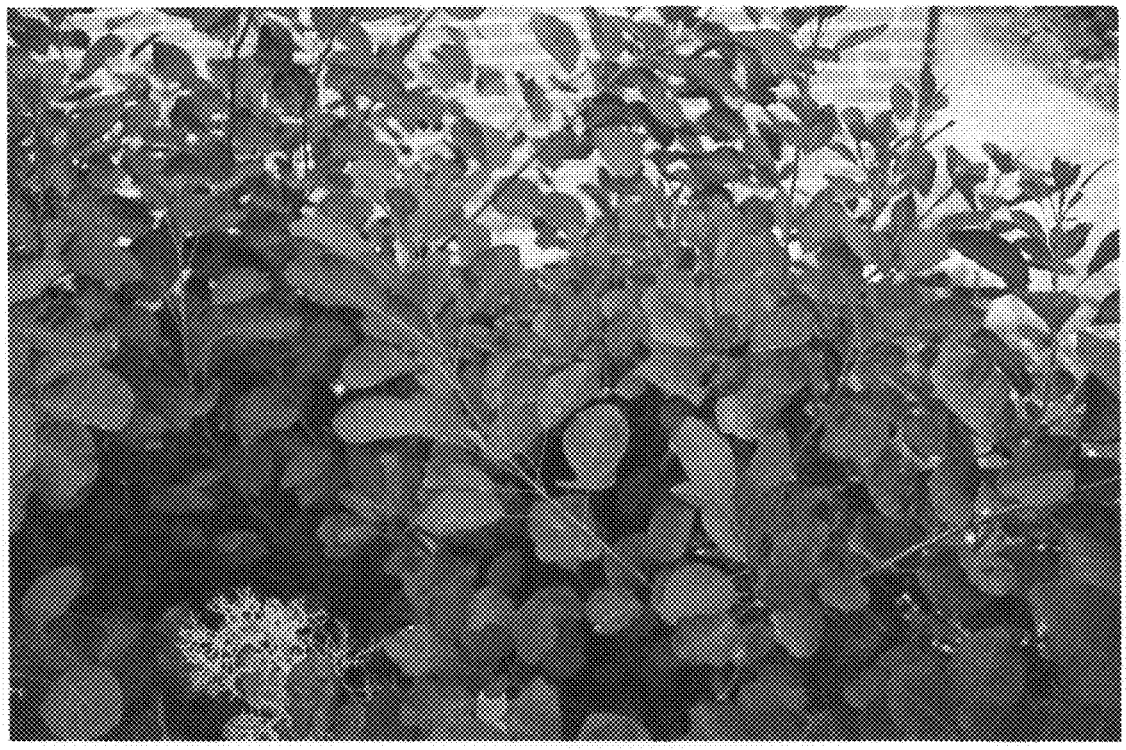
FIG. 2 illustrates a four year old plant of 'DUSKY MAIDEN' which has been established in the inventor's garden in a full sun location.
Figure 3:
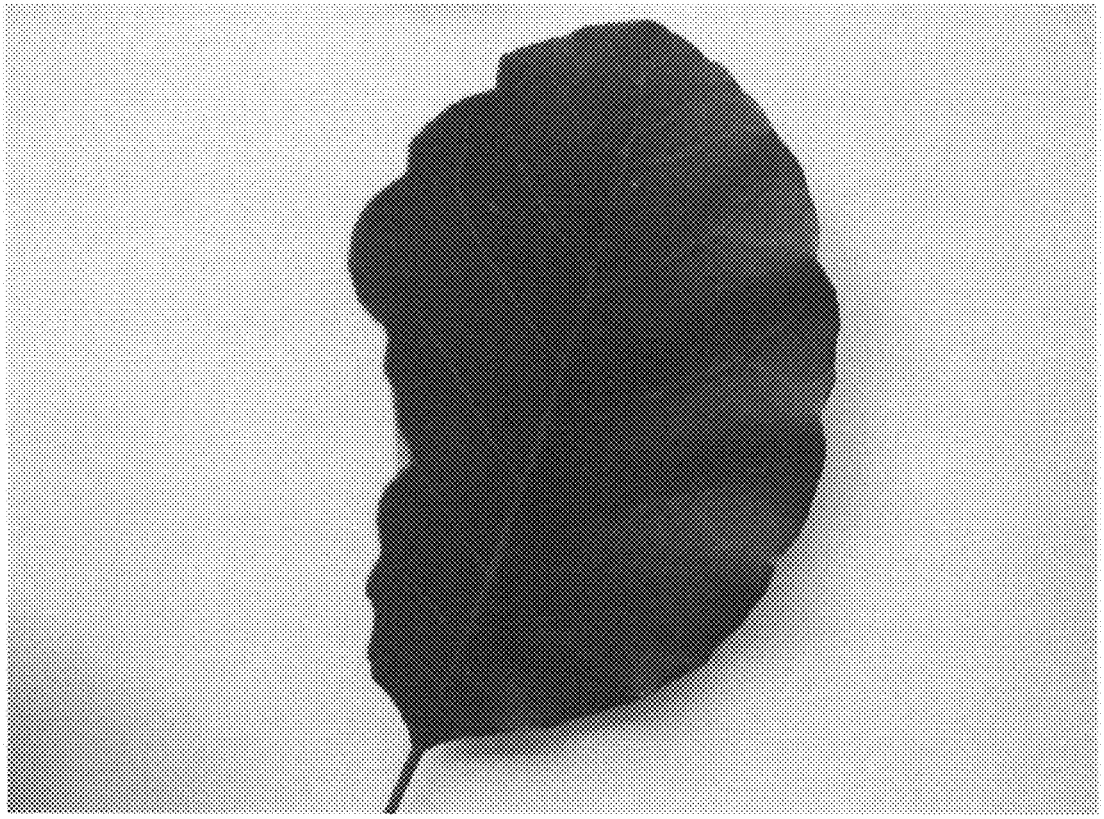
FIG. 3 illustrates the underside of a single leaf of 'DUSKY MAIDEN' showing the undulating margin and the red-purple coloration of the veins and petiole. This drawing is made from the plant illustrated in FIG. 2.
Figure 4:
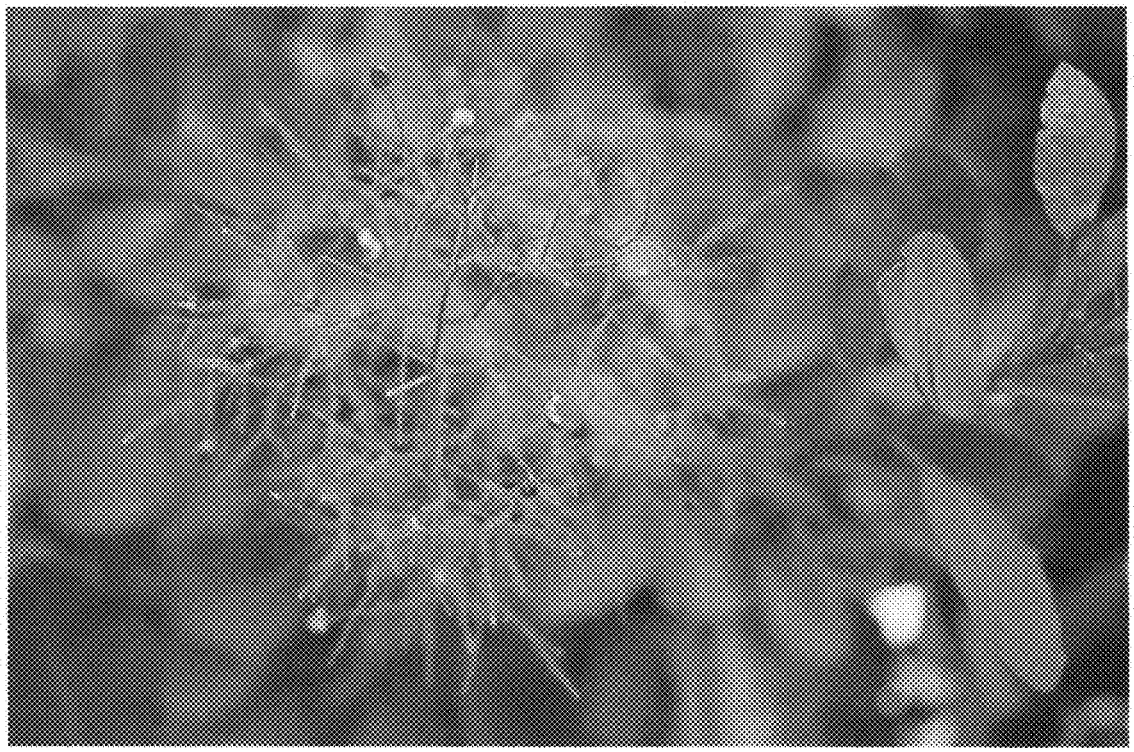
FIG. 4 illustrates the "smoky" inflorescence of 'DUSKY MAIDEN' after petal drop, showing the purplish hairs (pubescence) still present on the pedicels and the occasional red drupe which contains a single seed. This drawing is made from the plant illustrated in FIG. 2.

The drawings are made using conventional photographic techniques and although foliage colors in photographs may appear different from actual colors due to light reflectance, they are as accurate as possible by conventional photography.

BOTANICAL DESCRIPTION OF THE PLANT

The following is a detailed botanical description of the new cultivar of *Cotinus* named 'DUSKY MAIDEN'. Observations, measurements, values, and comparisons were collected in Hampshire, United Kingdom. The observed plant was four years old and had been growing in the open ground in full sun. 'DUSKY MAIDEN' has not been observed under all possible environmental conditions. The phenotype may vary with variations in the environment such as temperature and light level, without, however, any variance in genotype. Color references are made to The Royal Horticultural Society Colour Chart except where general terms of ordinary dictionary significance are used. The growing requirements are similar to the species and no growing problems have been observed.

Botanical classification: *Cotinus szechuanensis*×*coggygria* 'DUSKY MAIDEN'.

Common name: Smoke Bush.

Parentage:

*Female parent.*—*Cotinus szechuanensis.*

*Male parent.*—*Cotinus coggygria* 'Velvet Cloak'.

Propagation: Tissue culture and softwood cuttings.

Type: Large deciduous shrub.

Use: Landscape plant or container plant on patio.

Plant dimensions: 2 m to 2.5 m in height and width at 5–6 years.

Growth habit: Bushy.

Growth rate: Moderate.

Vigor: Average for *Cotinus* cultivars.

Seasonal interest: Spring, summer and fall foliage color.

Special needs: None observed.

Low temperature tolerance: Hardy to at least as cold as USDA Zone 7; hardiness testing continues.

Disease resistance and/or susceptibility: Not more resistant or susceptible to pests and diseases than other *Cotinus* varieties.

Soil types: Prefers dry or well-drained soils.

Light levels: Full sun is required to produce intense purple coloration.

Flowering season: Early summer.

Root system: Fibrous.

Propagation: Softwood cuttings root in 4–6 weeks at soil temperature of 20° C.

Cropping time: Plants will be of saleable size (height approximately 45 cm) 12–18 months after potting a rooted cutting.

Branching habit: Moderate free, mainly from upper half of 1 year old shoots unless cut back.

Branch angle at emergence: Approximately 30°.

First-year shoots:

*Color.*—187B.

*Cross-section.*—Round, solid.

*Dimensions.*—Approximately 40 cm in length and 4 mm in diameter.

*Surface.*—Smooth, weakly glaucous.

*Lenticels.*—Absent.

*Internode length.*—25 mm.

Second-year shoot:

*Texture.*—Slightly roughened.

*Color.*—199C.

Stem:

*Dimensions.*—1.5 m in length and 5 cm–8 cm in diameter.

*Appearance.*—Smooth, slightly glossy.

*Cross section.*—Rounded.

*Strength.*—Strong.

*Current year's growth.*—Ranges from 143C to 144A.

*Previous year's growth* (*bark present*).—N199A, N199C, both present.

*Pubescence.*—None.

Foliage:

*Leaf arrangement.*—Alternate.

*Compound or single.*—Single.

*Quantity of leaves per lateral branch.*—An average of 31.

*Leaves.*—Shape: Orbicular. Dimensions: An average of 6.0 cm in length and 4.2 cm in width. Margin: Entire, slightly undulate. Apex: Rounded. Base: Obtuse. Texture: Smooth, dull. Pubescence: None. Color (adaxial surface): 185A. Color (abaxial surface): 187A. Venation pattern: Pinnate. Vein color (adaxial surface): 187B. Vein color (abaxial surface) 183A. Durability to stress: High. Attachment: Petiolate.

*Petioles.*—Dimension: An average of 3.5 mm in length and 1.0 mm in diameter. Color: 185A. Foliage fragrance: None.

Inflorescence:

*Inflorescence type.*—Terminal thryse.

*Inflorescence dimensions.*—An average of 11.0 cm in height and 5.5 cm in width.

*Flowering season.*—May to early June.

*Peduncle.*—Dimensions: Length 15 mm; diameter 1.5 mm. Color: 185A. Pubescence: None.

*Pedicel.*—Dimensions: Length 3 mm; diameter <0.5 mm. Color: 178A. Pubescence: Present, prominent, numerous fine hairs, length approximately 0.5 mm, color appears closest to 181D.

*Bud.*—Shape: Spheroid. Dimension: Diameter 1.5 mm. Color: 163D.

Flowers: Single, persistent. Shape, aspect: Rotate, radiating from point of attachment. Fragrance: None.

*Calyx.*—Dimensions: diameter 2 mm; height <1 mm. Color (both surfaces): 146C. Pubescence: None.

*Sepals.*—6 in number. Dimensions: length 1 mm; width 0.5 mm. Shape: deltoid, apex acute, base truncate. Margin: Entire.

*Corolla.*—Dimensions: length <0.5 mm, width 2 mm. Shape: rotate. Number of petals: 5, unfused.

*Petals.*—Shape: Broad ovate, strongly recurved. Dimensions: length 1 mm; width 1 mm. Color (both surfaces): 160C. Surface: Smooth. Margins: Entire. Base: Obtuse. Apex: Acute.

*Stamens.*—Up to 5 present, but often absent or incompletely developed. When present, anthers red-purple, filaments purple but too small to color match.

*Pollen.*—Very sparse: insufficient to describe.

*Stigma.*—Shape: Cylindrical, broadening at tip. Length <0.5 mm; diameter <0.5 mm. Color: 149D.

*Ovary.*—Shape, position: Subreniform, superior. Dimensions: length 1 mm, width 1 mm. Color: 178A.

*Fruit.*—Ovoid drupe, length 3 mm, width 2 mm, color 42A.

*Seed.*—1 per drupe, round, diameter between 0.5 mm and 1 mm; color dark brown.

What is claimed is:

1. A new and distinct cultivar of *Cotinus* plant named 'DUSKY MAIDEN' as described and illustrated.

* * * * *